(12) United States Patent
Parr et al.

(10) Patent No.: US 10,716,699 B2
(45) Date of Patent: Jul. 21, 2020

(54) URINE COLLECTION SYSTEM FOR WOMEN

(71) Applicant: BP Solutions, LLC, Chickasha, OK (US)

(72) Inventors: Bradley Steven Parr, Chickasha, OK (US); James Alen Mohrbacker, El Mirage, AZ (US)

(73) Assignee: PB Solutions, LLC, Chickasha, OK (US)

( * ) Notice: Subject to any disclaimer, the term of this patent is extended or adjusted under 35 U.S.C. 154(b) by 0 days.

(21) Appl. No.: 16/680,583

(22) Filed: Nov. 12, 2019

(65) Prior Publication Data

US 2020/0078207 A1 Mar. 12, 2020

Related U.S. Application Data

(63) Continuation-in-part of application No. 15/216,143, filed on Jul. 21, 2016, now abandoned.

(60) Provisional application No. 62/197,941, filed on Jul. 28, 2015.

(51) Int. Cl.
*A61F 5/455* (2006.01)
*A61F 5/44* (2006.01)

(52) U.S. Cl.
CPC ............ *A61F 5/455* (2013.01); *A61F 5/4404* (2013.01)

(58) Field of Classification Search
CPC .............................. A61F 5/455; A61F 5/4404
See application file for complete search history.

(56) References Cited

U.S. PATENT DOCUMENTS

| 6,212,698 | B1 * | 4/2001 | Stingley | A61B 10/007 4/144.1 |
|---|---|---|---|---|
| 6,358,477 | B1 * | 3/2002 | Webb | A61B 10/007 4/144.1 |
| 6,775,852 | B1 * | 8/2004 | Alvarez | A61B 10/007 4/144.2 |
| 2007/0245486 | A1 * | 10/2007 | Battle | A61B 10/0038 4/661 |
| 2017/0027548 | A1 * | 2/2017 | Parr | A61B 10/007 |

* cited by examiner

*Primary Examiner* — Kristen Matter
(74) *Attorney, Agent, or Firm* — Martin S. High, P.C.

(57) ABSTRACT

Embodiments of the Urine Collection System for Women are comprised of a collection sheet, a top collection flange, a bottom collection flange, and a standard collection cup. The collection sheet forms an aperture onto which the top collection flange rests. The collection flange protrudes through the collection sheet and forms the bottom collection flange. The top collection flange and the bottom collection flange are integrally formed together to form the overall collection flange. The bottom collection flange forms the attachment means for the collection cup. The standard collection cup is a common medical urine collection cup that attaches to the bottom collection flange via an attachment means. The combined weight of the top collection flange and the bottom collection flange deflects the collection sheet into a conical shape thereby causing the collection sheet to serve as a funnel directing urine into the collection cup.

3 Claims, 5 Drawing Sheets

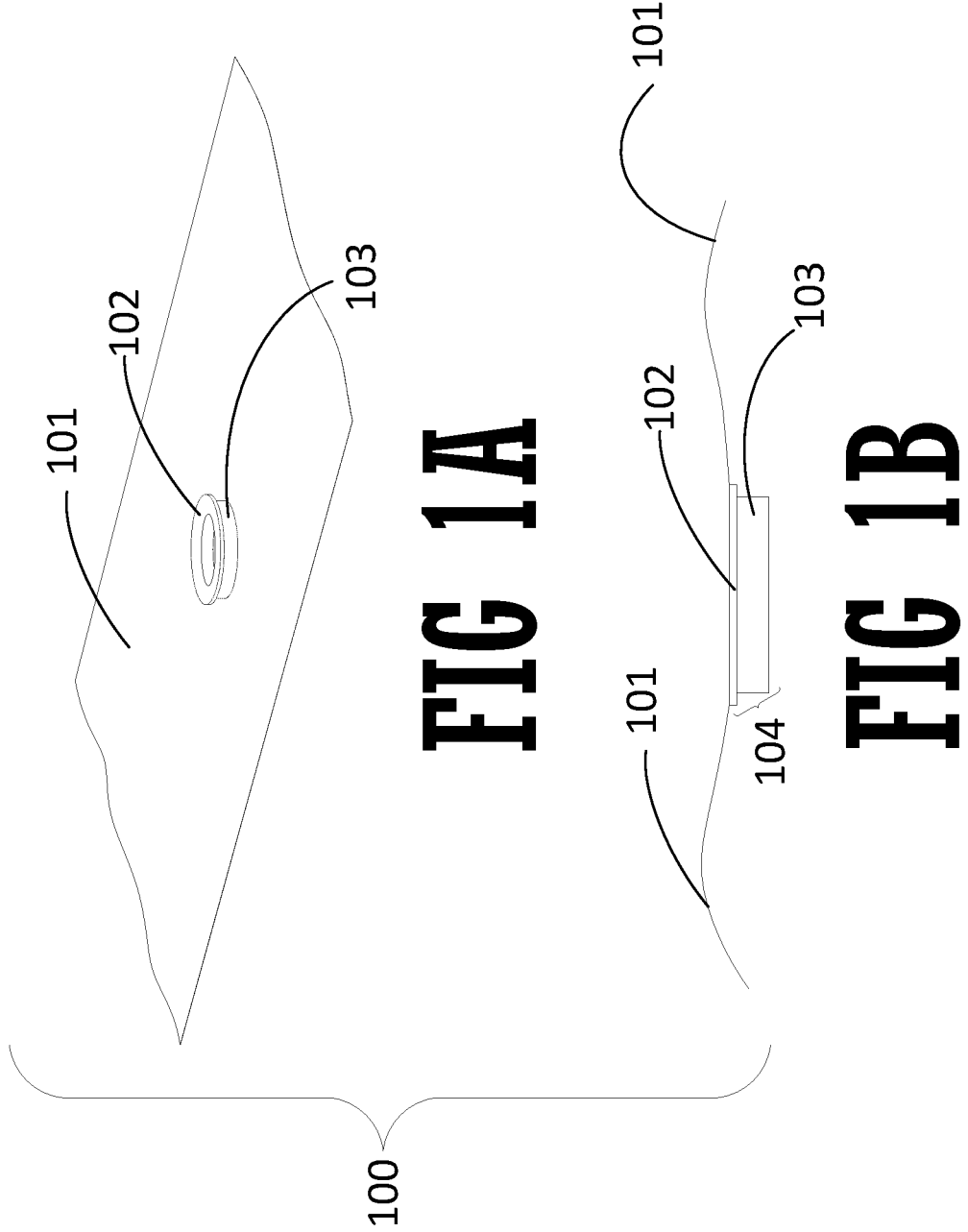

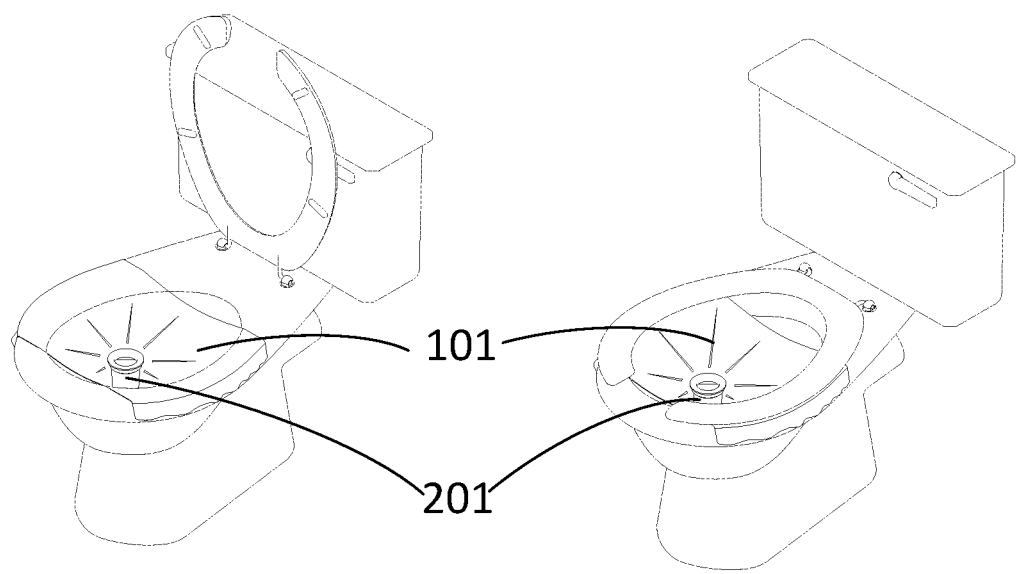
FIG 4A  FIG 4B
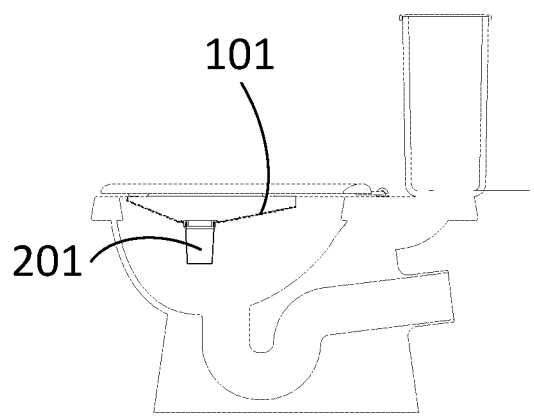
FIG 4C

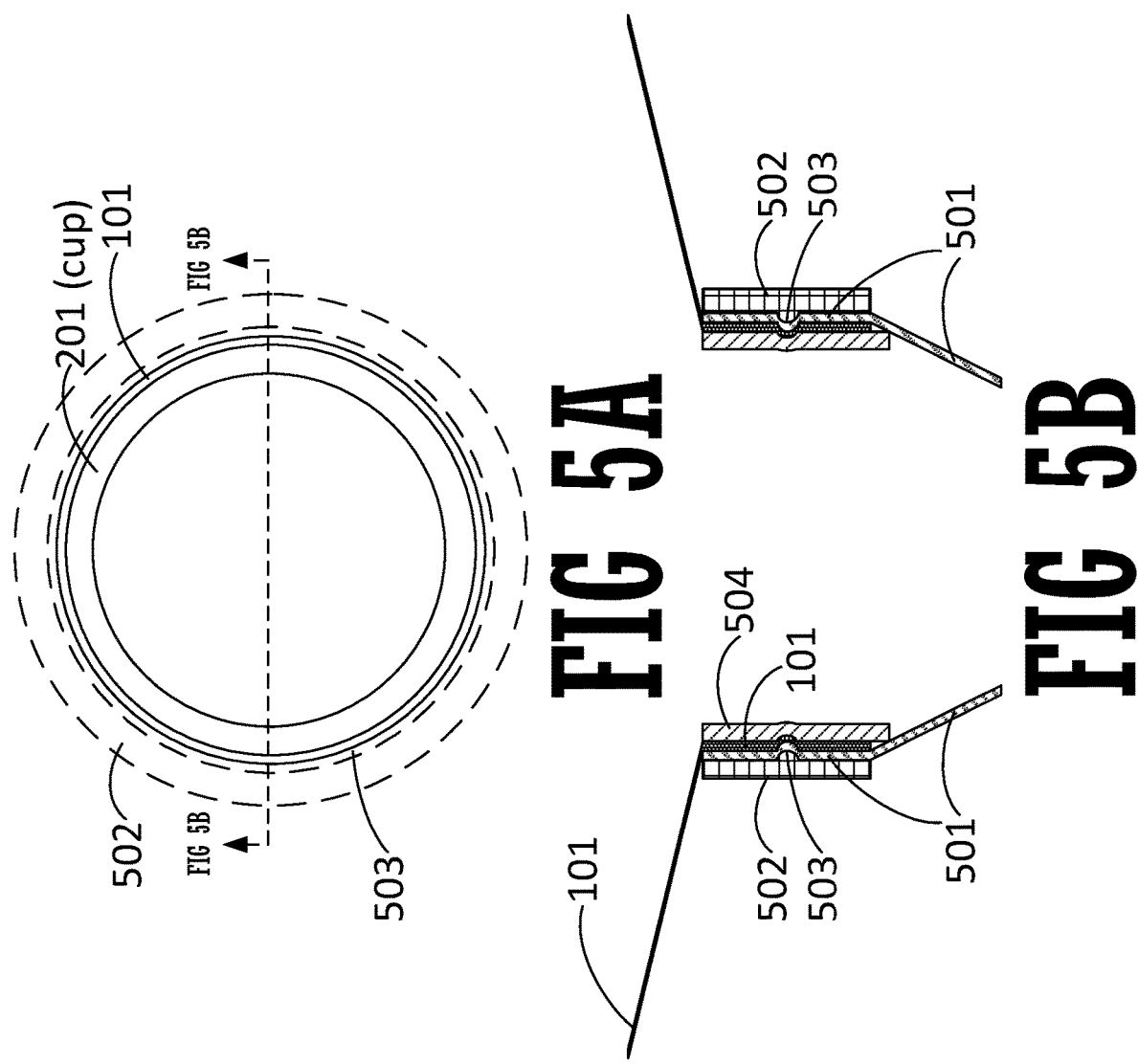

URINE COLLECTION SYSTEM FOR WOMEN

STATEMENT REGARDING FEDERALLY SPONSORED RESEARCH OR DEVELOPMENT

Not applicable

BACKGROUND OF THE EMBODIMENTS

Field of the Embodiments

The general field of the embodiments of the Urine Collection System for Women is healthcare. More specifically, the field of the embodiments relates to collection of urine samples for female patients.

Description of Prior Art

Women are at an anatomical disadvantage when it comes to providing urine samples for analysis for health care and drug testing purposes. The process of urine collection for women using cups in a similar manner to men can be frustrating, messy, and unsanitary. Some prior art devices intended to solve this problem typically involve the use of a pouch that adheres to the skin. Other prior art devices use pouches that are pressed against the skin, but not adhered to the skin. These devices are complicated to use and can irritate the skin and are still difficult for a woman to use. Further, the prior art techniques can easily lead to contaminated samples. The purpose of the Urine Collection System for Women is to provide an easy, sanitary means for women to collect urine for medical analysis.

SUMMARY OF THE EMBODIMENTS

Embodiments of the Urine Collection System for Women are comprised of a collection sheet, a top collection flange, a bottom collection flange, and a standard collection cup. The collection sheet is comprised of a thin polymeric sheet. In one embodiment of the Urine Collection System for Women, the thin polymeric sheet is comprised of polypropylene. The collection sheet forms an aperture onto which the top collection flange rests. The collection flange protrudes through the collection sheet and forms the bottom collection flange. The top collection flange and the bottom collection flange are integrally formed together to form the overall collection flange. The bottom collection flange forms the attachment means for the collection cup. In one embodiment of the Urine Collection System for Women, the attachment means is a resistance fit. In one embodiment of the Urine Collection System for Women, the collection cup is secured by a resistance fit to the bottom collection flange. In another embodiment of the Urine Collection System for Women, the attachment means is a threaded connection, and the collection cup is threadedly connected to the bottom collection flange.

The standard collection cup is a common medical urine collection cup that attaches to the bottom collection flange via an attachment means. The attachment means is comprised of either a resistance fit or a threaded connection. The standard collection cup is attached to the bottom collection flange and serves to collect urine. The combined weight of the top collection flange and the bottom collection flange deflects the collection sheet into a conical shape thereby causing the collection sheet to serve as a funnel directing urine into the collection cup.

There has thus been outlined, rather broadly, the more important features of the embodiments of the Urine Collection System for Women in order that the detailed description thereof that follows may be better understood, and in order that the present contribution to the art may be better appreciated. There are, of course, additional features of the embodiments that will be described hereinafter and which will form the subject matter of the claims appended hereto.

In this respect, before explaining at least one embodiment of the embodiments in detail, it is to be understood that the embodiment is not limited in this application to the details of construction and to the arrangements of the components set forth in the following description or illustrated in the drawings. The embodiment or embodiments are capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be used as a basis for the designing of other structures, methods and systems for carrying out the several purposes of the embodiments. Additional benefits and advantages of the embodiments will become apparent in those skilled in the art to which the present embodiments relates from the subsequent description of the preferred embodiment and the appended claims, taken in conjunction with the accompanying drawings. It is important, therefore, that the claims be regarded as including such equivalent constructions insofar as they do not depart from the spirit and scope of the embodiments.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the embodiments of the application which is measured by the claims, nor is it intended to be limiting as to the scope of the embodiments in any way.

BRIEF DESCRIPTION OF THE DRAWINGS

FIG. 1A is a perspective view of an embodiment of the Urine Collection System for Women; FIG. 1B is a side view of an embodiment of the Urine Collection System for Women.

FIG. 4A is a schematic view of an embodiment of the Urine Collection System for Women showing how the Urine Collection System for Women engages with a toilet with the toilet seat raised; FIG. 4B is a schematic view of an embodiment of the Urine Collection System for Women showing how the Urine Collection System for Women engages with a toilet with the toilet seat lowered; FIG. 4C is a side view of an embodiment of the Urine Collection System for Women showing how the Urine Collection System for Women engages with a toilet.

FIG. 5A is a schematic top view of an embodiment of the Urine Collection System for Women; FIG. 5B is a schematic top view of an embodiment of the Urine Collection System for Women.

DETAILED DESCRIPTION OF THE PREFERRED EMBODIMENTS

Figures 2A, 2B:
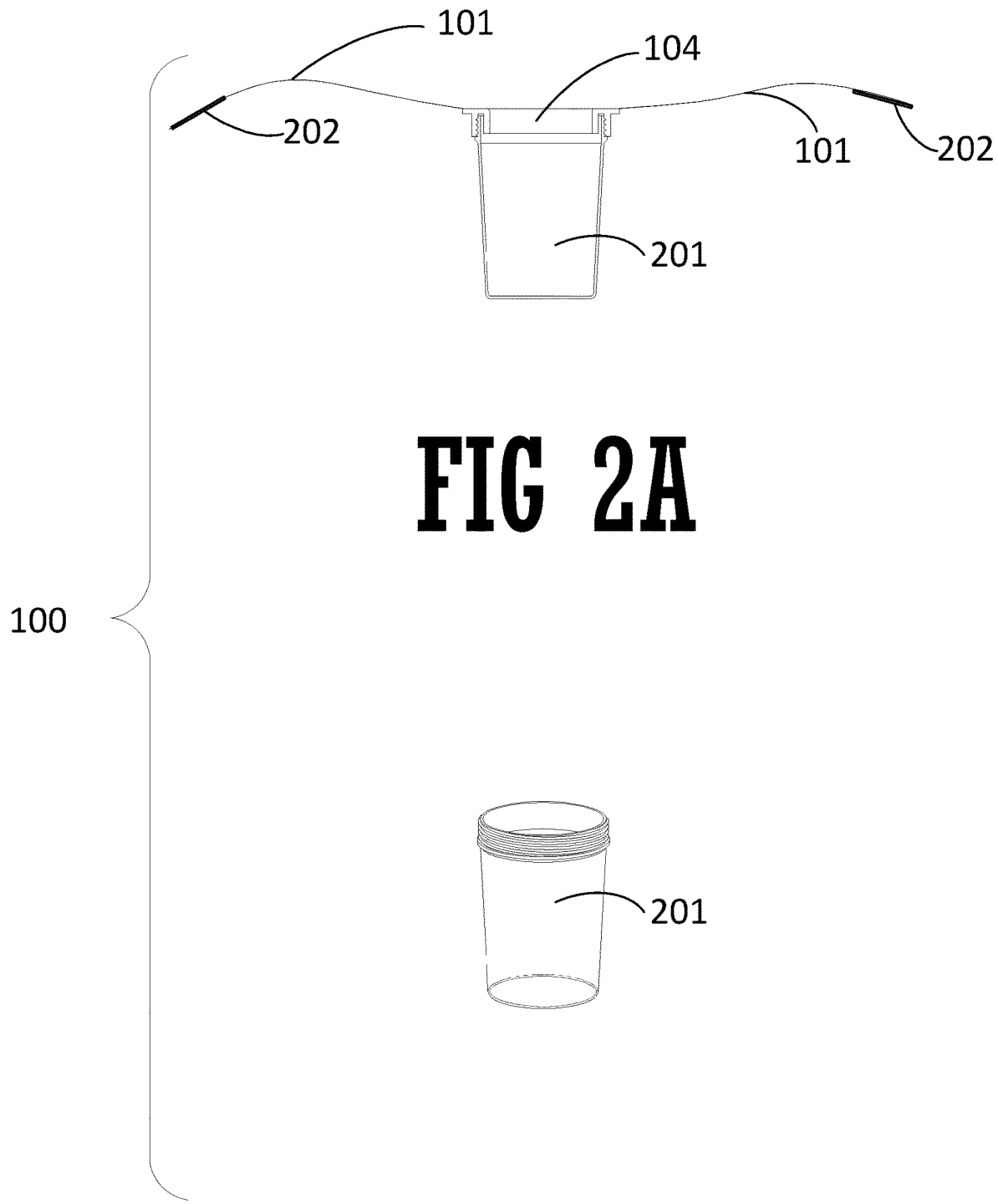
FIG. 2A is a side view of an embodiment of the Urine Collection System for Women showing the collection cup attached.
FIG. 2B is a perspective view of an embodiment of the standard collection cup that engages with the Urine Collection System for Women.
Figures 3A, 3B:
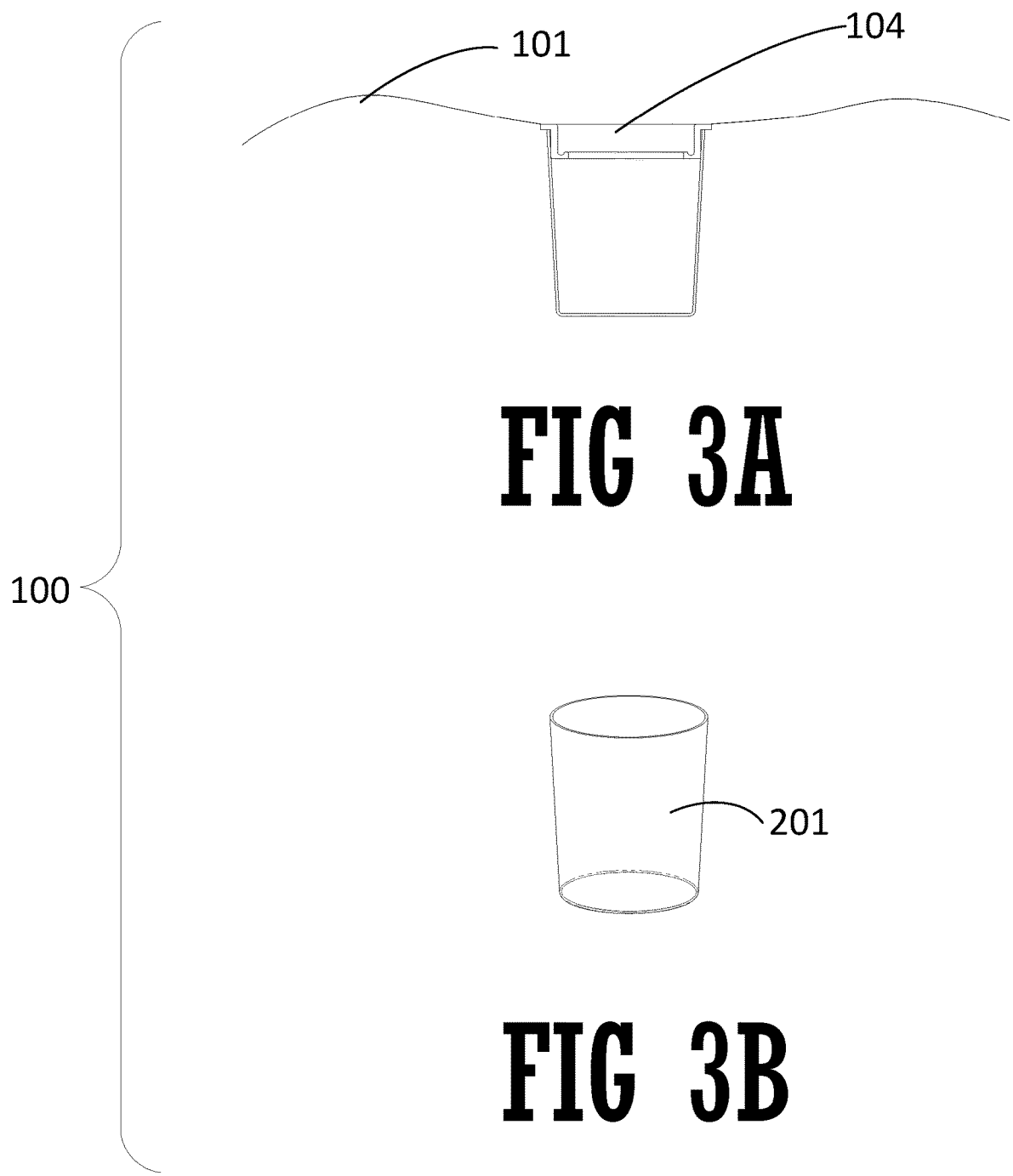
FIG. 3A is a side view of an embodiment of the Urine Collection System for Women showing how the standard collection cup engages with the Urine Collection System for Women.
FIG. 3B is a side view of an embodiment of the standard collection cup that engages with the Urine Collection System for Women.

Embodiments of the Urine Collection System for Women 100 are comprised of a collection sheet 101, a top collection flange 102, a bottom collection flange 103, and a collection cup 201.

The collection sheet 101 is comprised of a thin polymeric sheet. In one embodiment of the Urine Collection System for Women, the thin polymeric sheet is comprised of polypropylene. The collection sheet 101 is adhered to the top collection flange 102 using either thermal forming (melting) of the collection sheet 101 to the top of the top collection flange 102 or by the use of adhesive. The collection sheet 101 forms an aperture onto which the top collection flange 102 rests. The collection flange protrudes through the collection sheet 101 and forms the bottom collection flange 103. The top collection flange 102 and the bottom collection flange 103 are integrally formed together to form the overall collection flange 104. The bottom collection flange 103 forms the attachment means for the collection cup 201. In one embodiment of the Urine Collection System for Women, the attachment means is a resistance fit. The collection cup 201 is secured by a resistance fit to the bottom collection flange 103. In another embodiment of the Urine Collection System for Women, the attachment means is a threaded connection. In this embodiment, the collection cup 201 is threadedly connected to the bottom collection flange 103.

The collection cup 201 is a common medical urine collection cup that attaches to the bottom collection flange 103 via an attachment means. The collection cup 201 may also be a standard medical collection cup. The attachment means is comprised of either a resistance fit or a threaded connection. The collection cup 201 is attached to the bottom collection flange 103 and serves to collect urine. The combined weight of the top collection flange 102 and the bottom collection flange 103 deflects the collection sheet 101 into a conical shape thereby causing the collection sheet 101 to serve as a funnel directing urine into the collection cup 201.

In another embodiment of the Urine Collection System for Women, the attachment means for the urine collection cup is a resistance fit with a polymeric adhesive means around the perimeter of the opening of the collection flange. The collection cup 201 in this embodiment does not employ threads to engage with the collection flange 102, but rather the polymeric adhesive retains the collection cup in place in place of threads. Further, the outside diameter of the cup is essentially the same as in the inside diameter of the flange, so the cup is engaged by a resistance fit.

In another embodiment of the Urine Collection System for Women, adhesive means 202 are located on the edges of the collection sheet 101. The adhesive means comprises a silicone polymer temporary adhesive or other type of temporary adhesive system. The adhesive means 202 provides a means of securing the collection sheet to at toilet seat, In a best mode of use of the Urine Collection System for Women, the user secures the collection cup 201 onto the bottom collection flange 103 either through a resistance fit or a threaded connection. The collection sheet 101 is placed onto a toilet seat. In the embodiment of the Urine Collection System for Women that comprises an adhesive means 202, that adhesive means is used to additionally secure the collection sheet 101 to the toilet seat. The collection cup 201 should be centered roughly in the middle of the toilet seat opening. The user then sits on the toilet seat and produces urine. The urine then flows to the center of the collection sheet 101 and flows into the collection cup 201. The user then removes the collection sheet 101 from the toilet, removes the collection cup 201 from the bottom collection flange 103, and places the collection cup lid on the collection cup 201 for storage, transport, or use by the medical facility.

In another embodiment, the Urine Collection System for Women 100 is comprised of a collection sheet 101, an elastomeric ring 501, an outer ring 502 comprising a raised ring 503 that forms a seal among the collection sheet 101, the elastomeric ring 501, and an inner ring 504. In this embodiment, non-standard sized collection cups with or without threads can be used. The outer ring 502, the inner ring 504, and the raised ring 503 operate to seal the collection sheet 101 and the elastomeric ring 501 against the inner ring 504. A collection cup of any size can be inserted into either the center of the elastomeric ring 501 from above and pushed downward to seal or inserted from the underneath by elongating the elastomeric ring 501 around the outer edge of the cup and rotating the cup upwardly until the cup reaches the bottom of inner ring 504.

What we claimed is:
1. A urine collection system comprising:
a collection sheet configured to be secured to a toilet;
an inner ring;
an outer ring comprising a raised ring located on an inner surface of the outer ring; and
an elastomeric ring;
wherein the collection sheet and elastomeric ring are secured between the inner and outer rings such that the raised ring of the outer ring forms a seal with the collection sheet, the elastomeric ring and the inner ring; and
wherein the elastomeric ring extends past a bottom of the inner and out rings and is configured to hold a collection cup such that a user can deposit a urine sample into the collection cup while the system is secured to the toilet.
2. The urine collection system of claim 1, wherein the collection sheet is made of polypropylene.
3. The urine collection system of claim 1, wherein the collection cup can be inserted into the elastomeric ring from either a top or bottom side of the elastomeric ring.

\* \* \* \* \*

UNITED STATES PATENT AND TRADEMARK OFFICE
CERTIFICATE OF CORRECTION

PATENT NO. : 10,716,699 B2
APPLICATION NO. : 16/680583
DATED : July 21, 2020
INVENTOR(S) : Bradley S. Parr et al.

Page 1 of 1

It is certified that error appears in the above-identified patent and that said Letters Patent is hereby corrected as shown below:

On the Title Page

Item (73) Assignee: change "PB Solutions, LLC," to read as --BP Solutions, LLC--.

Signed and Sealed this
Seventh Day of October, 2025

John A. Squires
*Director of the United States Patent and Trademark Office*